United States Patent [19]
de la Fuente

[11] Patent Number: 5,531,706
[45] Date of Patent: Jul. 2, 1996

[54] SAFETY SYRINGE

[75] Inventor: Ricardo L. de la Fuente, Coral Gables, Fla.

[73] Assignee: Protecs Syringes International Corporation, Miami, Fla.

[21] Appl. No.: 214,618

[22] Filed: Mar. 18, 1994

Related U.S. Application Data

[63] Continuation-in-part of Ser. No. 679,753, Apr. 3, 1991, Pat. No. 5,306,258.

[51] Int. Cl.$^6$ ..................................................... A61M 5/32
[52] U.S. Cl. .......................................... 604/198; 604/110
[58] Field of Search .................................... 604/110, 187, 604/192, 198, 199, 227, 228, 263, 229, 232

[56] References Cited

U.S. PATENT DOCUMENTS

| | | |
|---|---|---|
| 2,571,653 | 10/1951 | Bastien . |
| 2,745,403 | 5/1956 | Goldberg ................................ 604/232 |
| 3,115,135 | 12/1963 | Sarnoff .................................. 604/232 |
| 4,356,822 | 11/1982 | Winstead-Hall . |
| 4,425,210 | 1/1984 | Sampson et al. . |
| 4,573,976 | 3/1986 | Sampson et al. . |
| 4,610,667 | 9/1986 | Pedicano et al. . |
| 4,631,057 | 12/1986 | Mitchell . |
| 4,636,201 | 1/1987 | Ambrose et al. . |
| 4,639,249 | 1/1987 | Larson .................................... 604/198 |
| 4,664,259 | 5/1987 | Landis . |
| 4,701,165 | 10/1987 | DeHaitre ................................ 604/228 |
| 4,723,943 | 2/1988 | Spencer . |
| 4,735,618 | 4/1988 | Hagen . |
| 4,738,663 | 4/1988 | Bogan . |
| 4,747,830 | 5/1988 | Gloyer et al. . |
| 4,747,837 | 5/1988 | Hauck . |
| 4,767,413 | 8/1988 | Haber et al. ........................... 604/232 |
| 4,772,272 | 9/1988 | McFarland . |
| 4,790,827 | 12/1988 | Haber et al. . |
| 4,801,295 | 1/1989 | Spencer ................................. 604/198 |
| 4,842,587 | 6/1989 | Poncy . |
| 4,846,796 | 7/1989 | Carrell et al. . |
| 4,850,961 | 7/1989 | Wanderer et al. . |
| 4,850,994 | 7/1989 | Zerbst et al. . |
| 4,892,523 | 1/1990 | Haber et al. . |
| 4,898,590 | 2/1990 | Andors . |
| 4,900,311 | 2/1990 | Stern et al. . |
| 4,911,693 | 3/1990 | Paris . |
| 4,915,695 | 4/1990 | Koobs . |
| 4,915,696 | 4/1990 | Feimer . |
| 4,915,697 | 4/1990 | DuPont . |
| 4,915,698 | 4/1990 | Levenson . |
| 4,915,699 | 4/1990 | Kornberg . |
| 4,915,700 | 4/1990 | Noonan, Jr. . |
| 4,915,701 | 4/1990 | Halkyard . |
| 4,915,702 | 4/1990 | Haber . |
| 4,917,672 | 4/1990 | Terndrup et al. . |
| 4,917,673 | 4/1990 | Coplin . |
| 4,917,679 | 4/1990 | Kronner . |
| 4,931,040 | 6/1990 | Haber et al. ........................... 604/232 |
| 4,969,877 | 11/1990 | Kornberg . |

(List continued on next page.)

FOREIGN PATENT DOCUMENTS 0350186  1/1990  European Pat. Off. .

Primary Examiner—John D. Yasko
Assistant Examiner—Ronald K. Stright, Jr.
Attorney, Agent, or Firm—Dilworth & Barrese

[57] ABSTRACT

A syringe is disclosed which includes a needle body having a proximal end and a distal end, a needle attached to the distal end of the needle body, a plunger for drawing fluid into the needle body through the needle, and a protective sheath configured and dimensioned to be positioned about the needle body and movable between a first distal position whereby the needle is shielded by the sheath and a proximal position whereby the needle is exposed. A system of slots and pegs is provided to releasably retain the protective sheath in the first distal position and to releasably retain the protective sheath in the proximal position. Also disclosed is an improved locking system which includes a pair of opposed locking struts fixed to the sheath at respective proximal and distal ends thereof to securely retain and lock the protective sheath in a second distal position after use to prevent unwanted contact with the needle.

20 Claims, 16 Drawing Sheets

U.S. PATENT DOCUMENTS

| | | |
|---|---|---|
| 4,973,316 | 11/1990 | Dysarz . |
| 4,973,317 | 11/1990 | Bobrove . |
| 4,973,318 | 11/1990 | Holm et al. . |
| 4,994,045 | 2/1991 | Ranford . |
| 5,013,302 | 5/1991 | Schmidt . |
| 5,019,043 | 5/1991 | Pastor et al. . |
| 5,019,044 | 5/1991 | Tsao . |
| 5,019,051 | 5/1991 | Hake . |
| 5,057,079 | 10/1991 | Tiemann et al. . |
| 5,057,087 | 10/1991 | Harmon . |
| 5,059,185 | 10/1991 | Ryan . |
| 5,106,379 | 4/1992 | Leap . |
| 5,399,170 | 3/1995 | Whitley ................................ 604/263 |

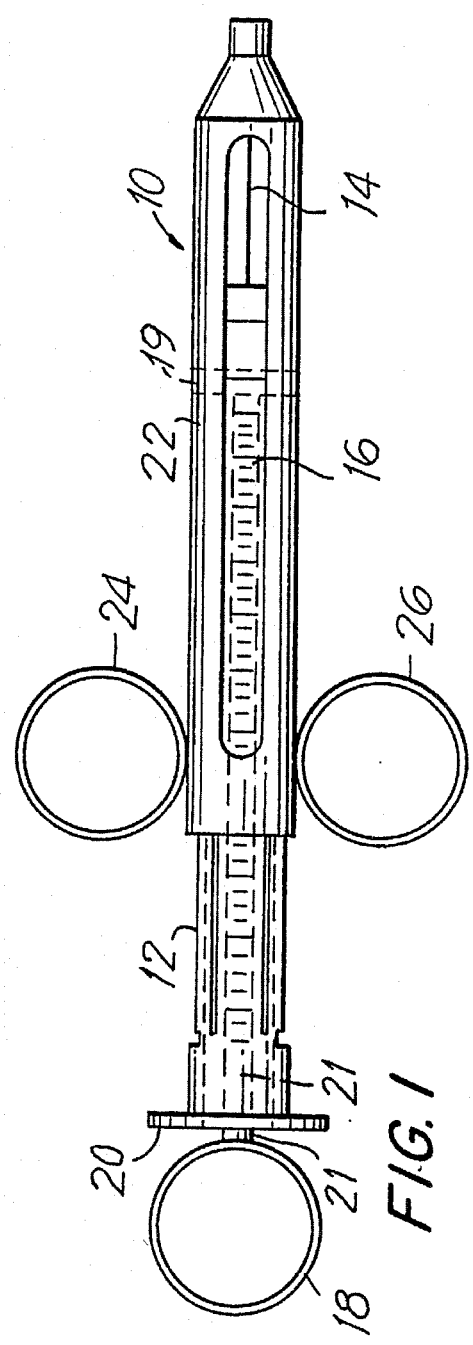
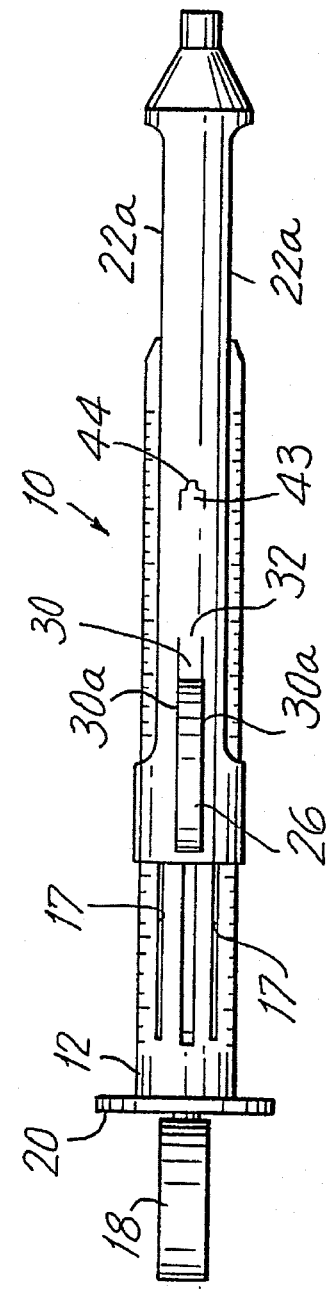
FIG. 1
FIG. 2

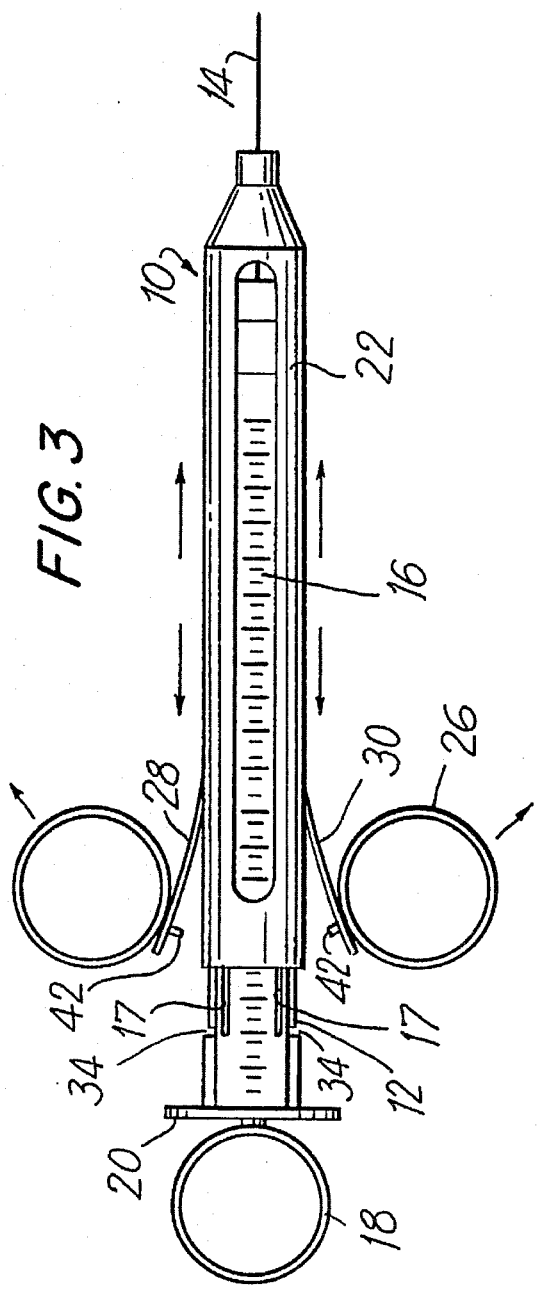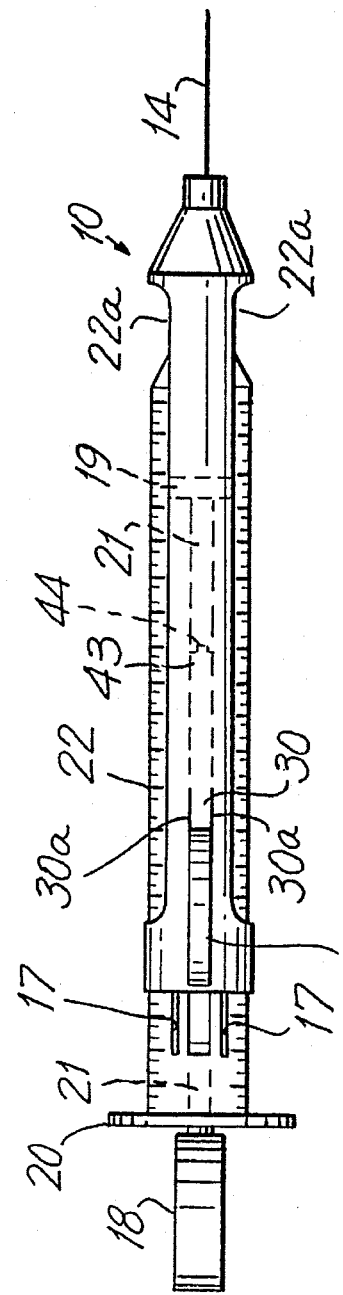

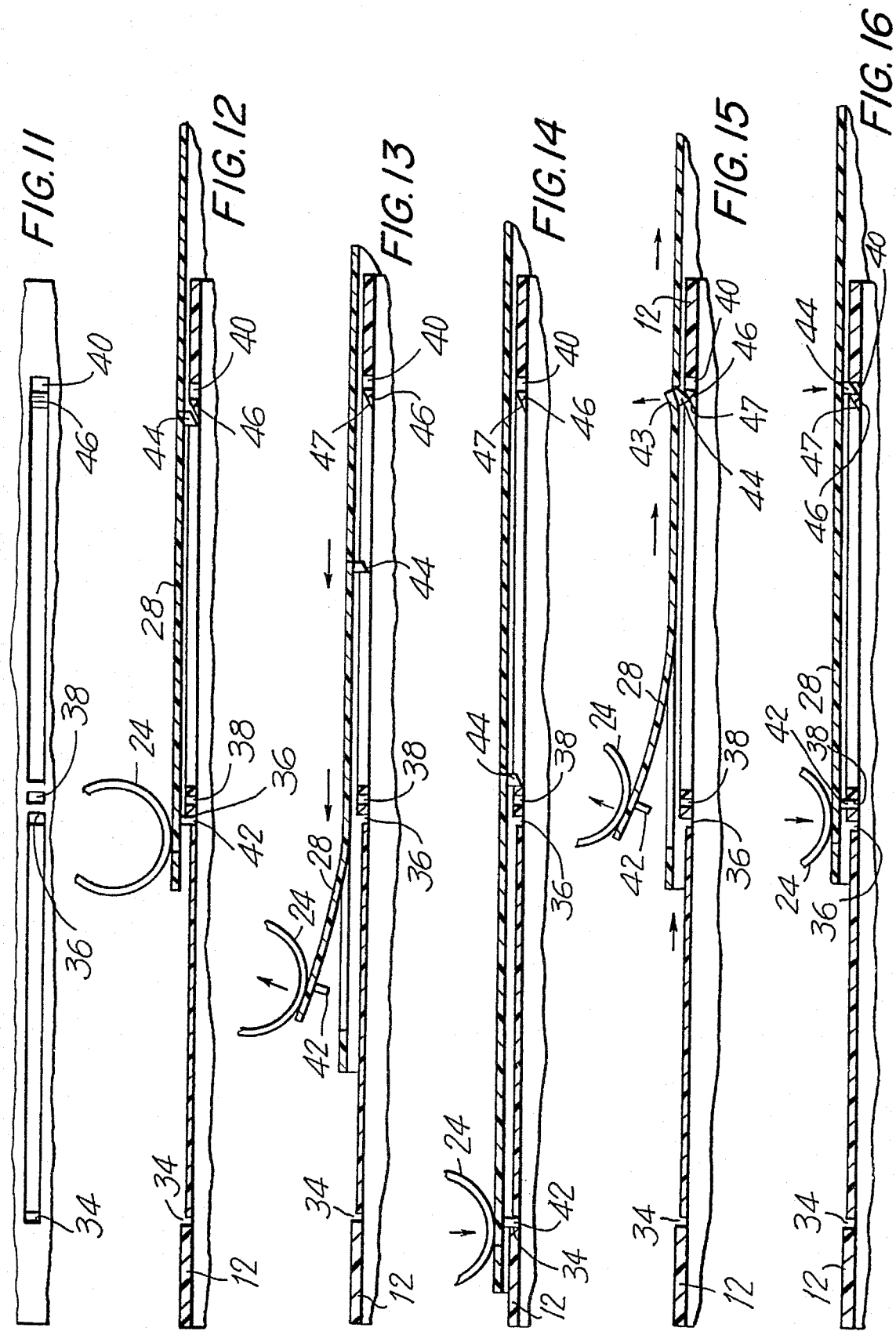

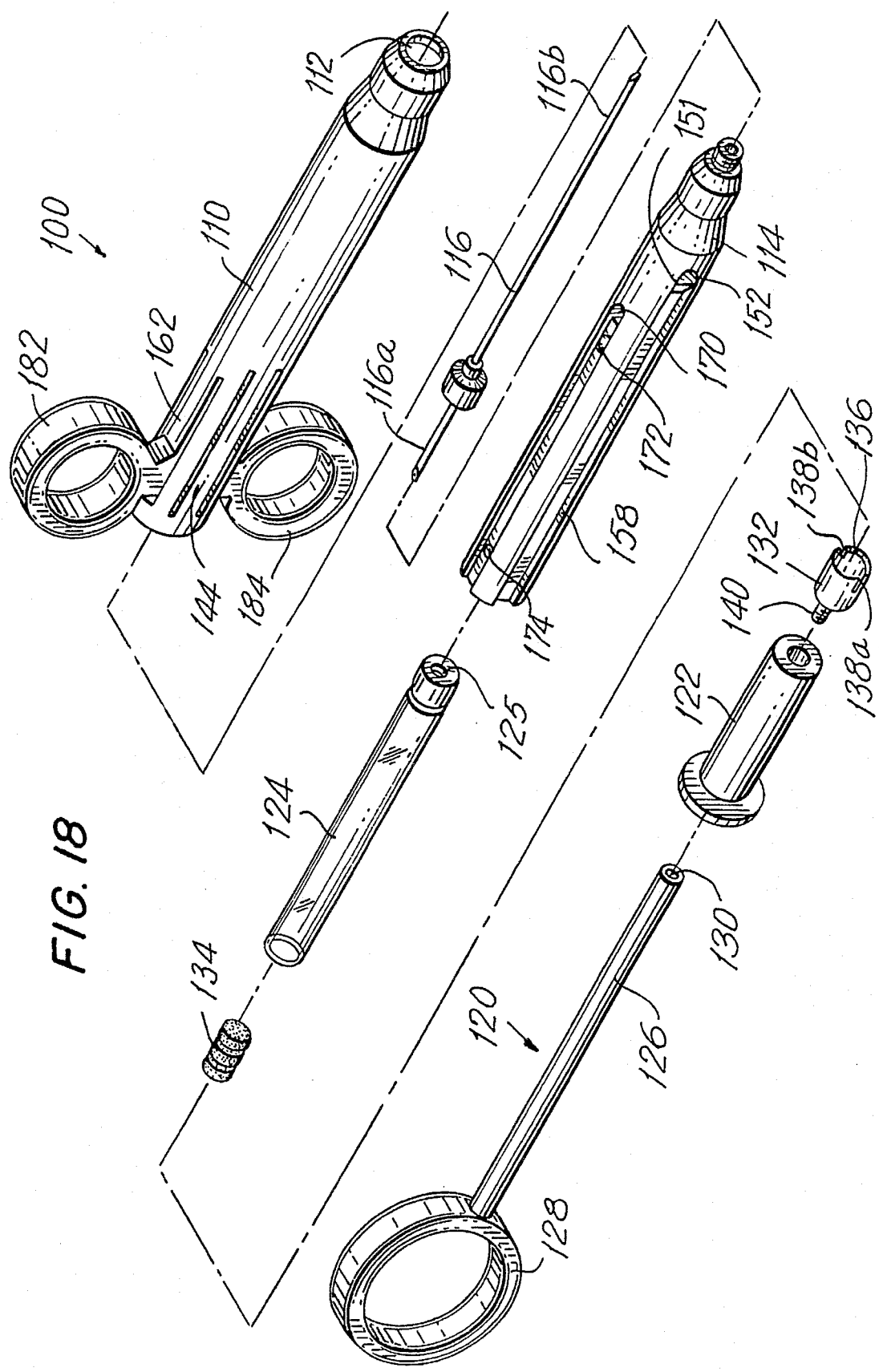

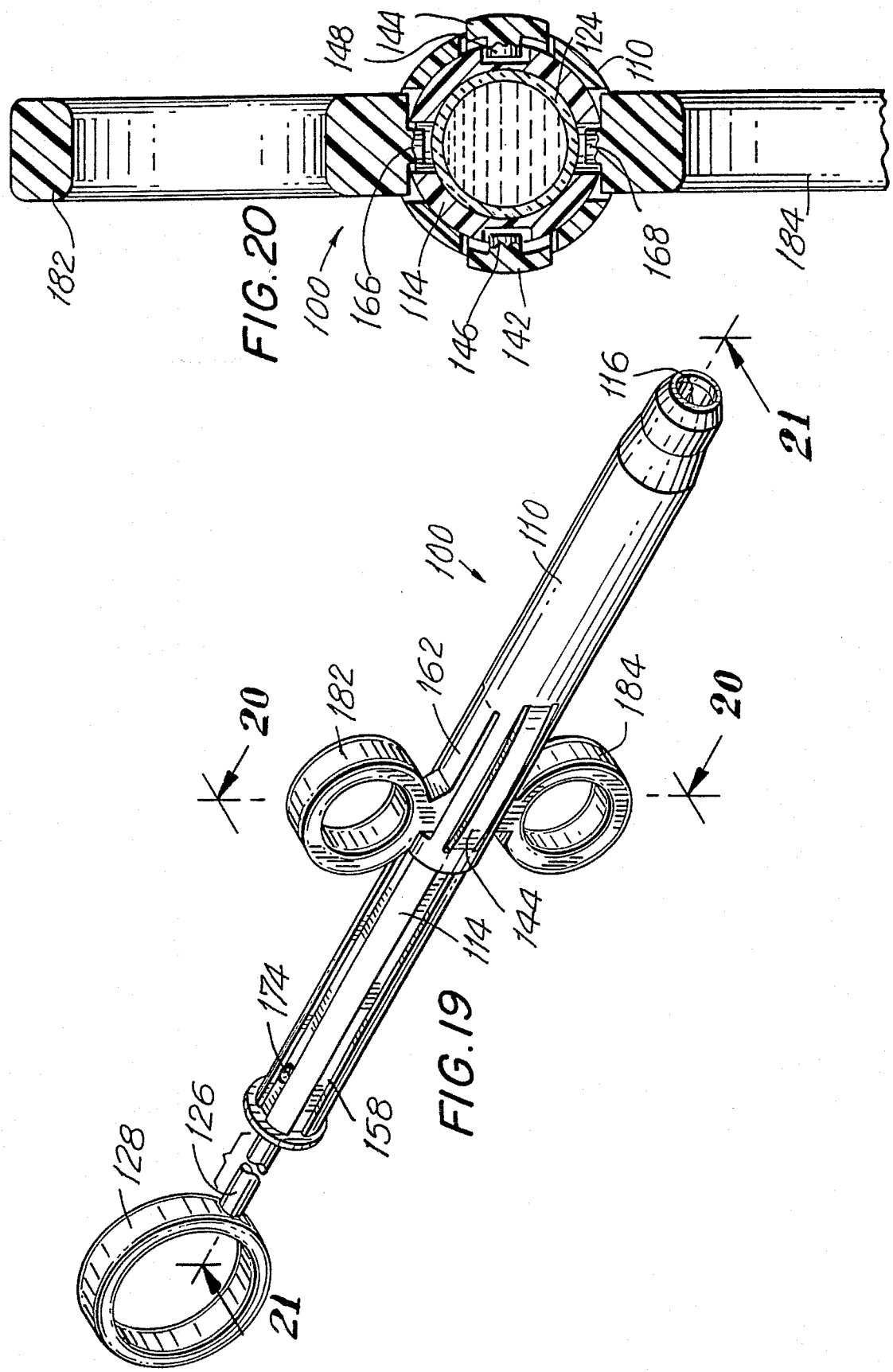

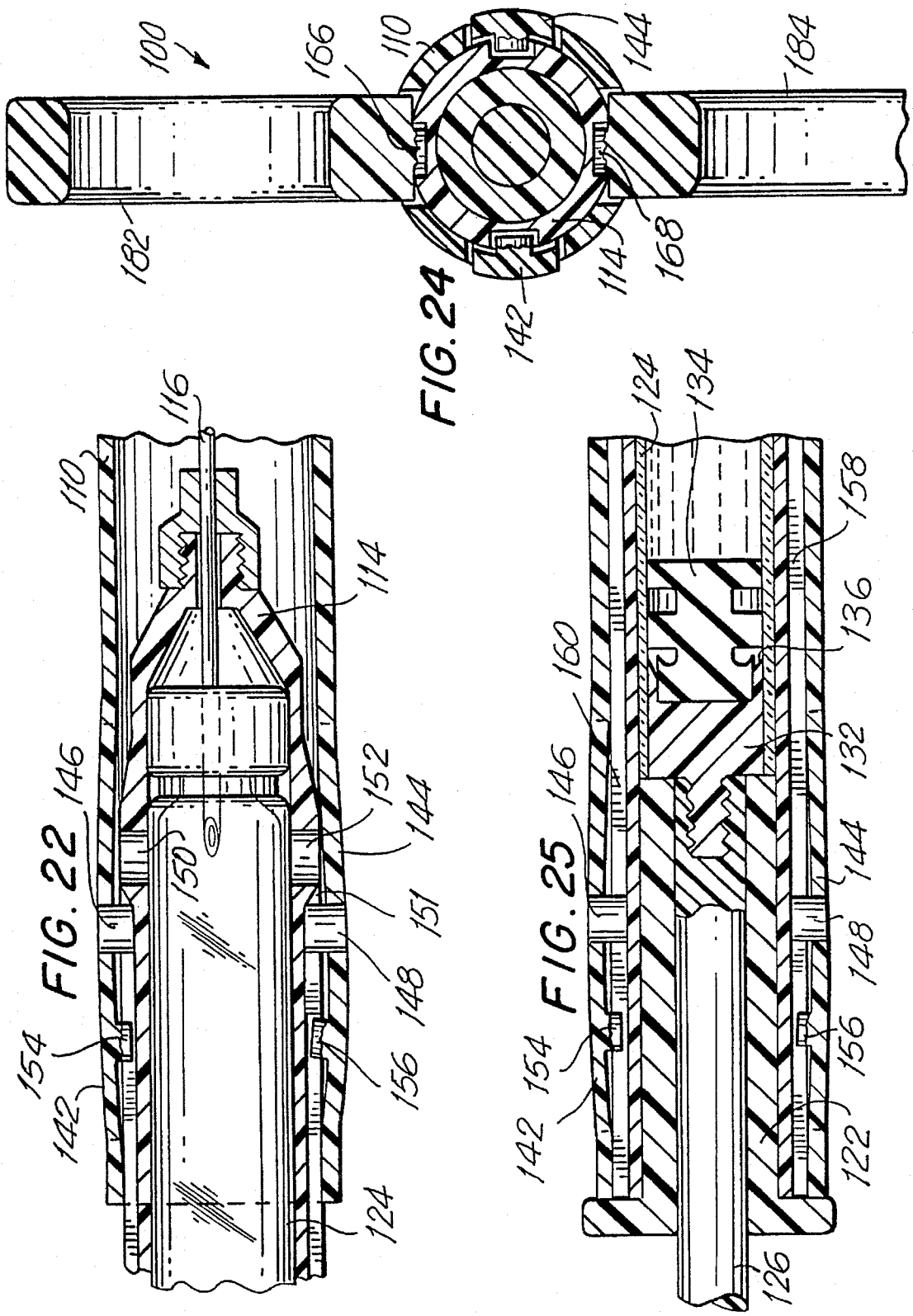

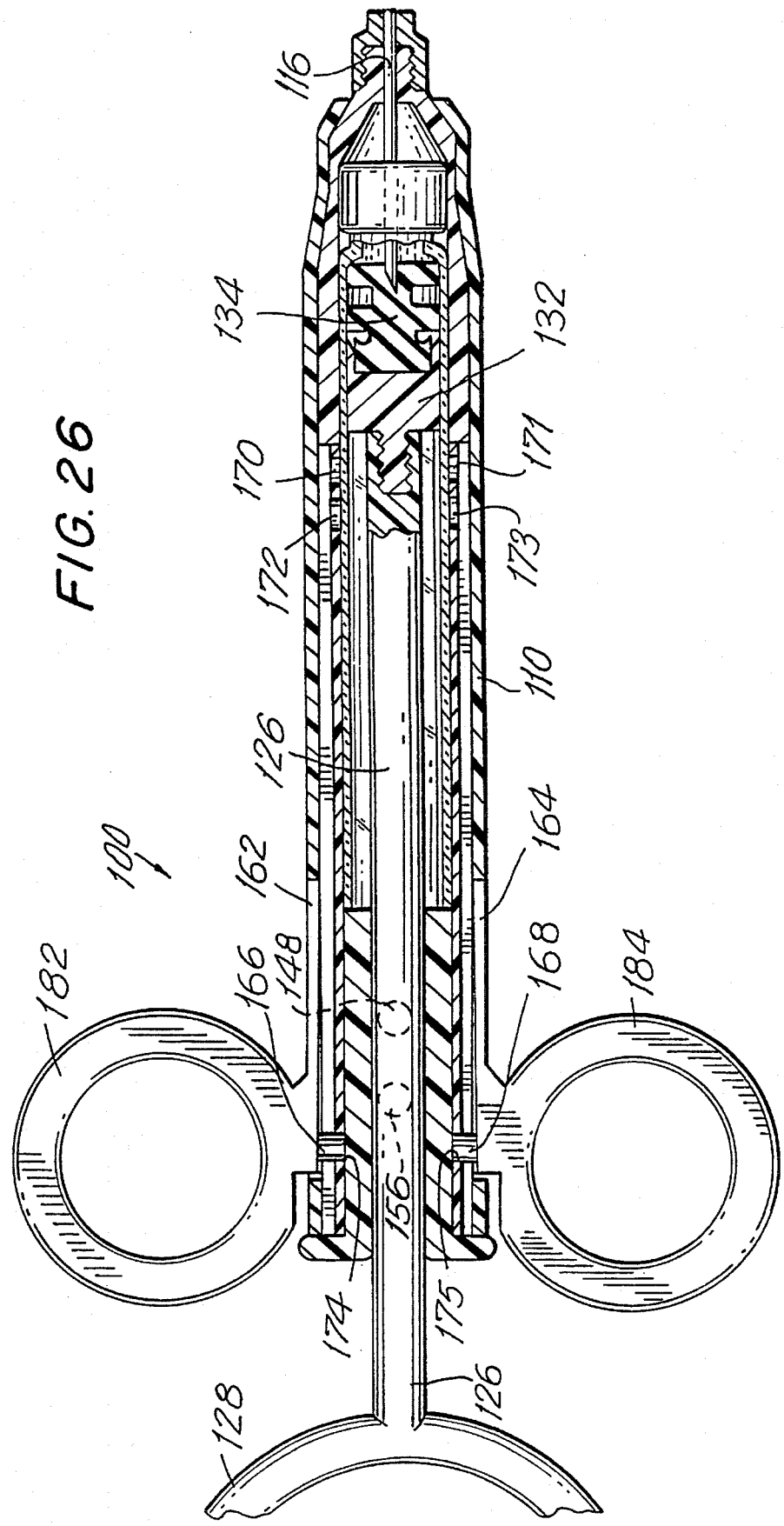

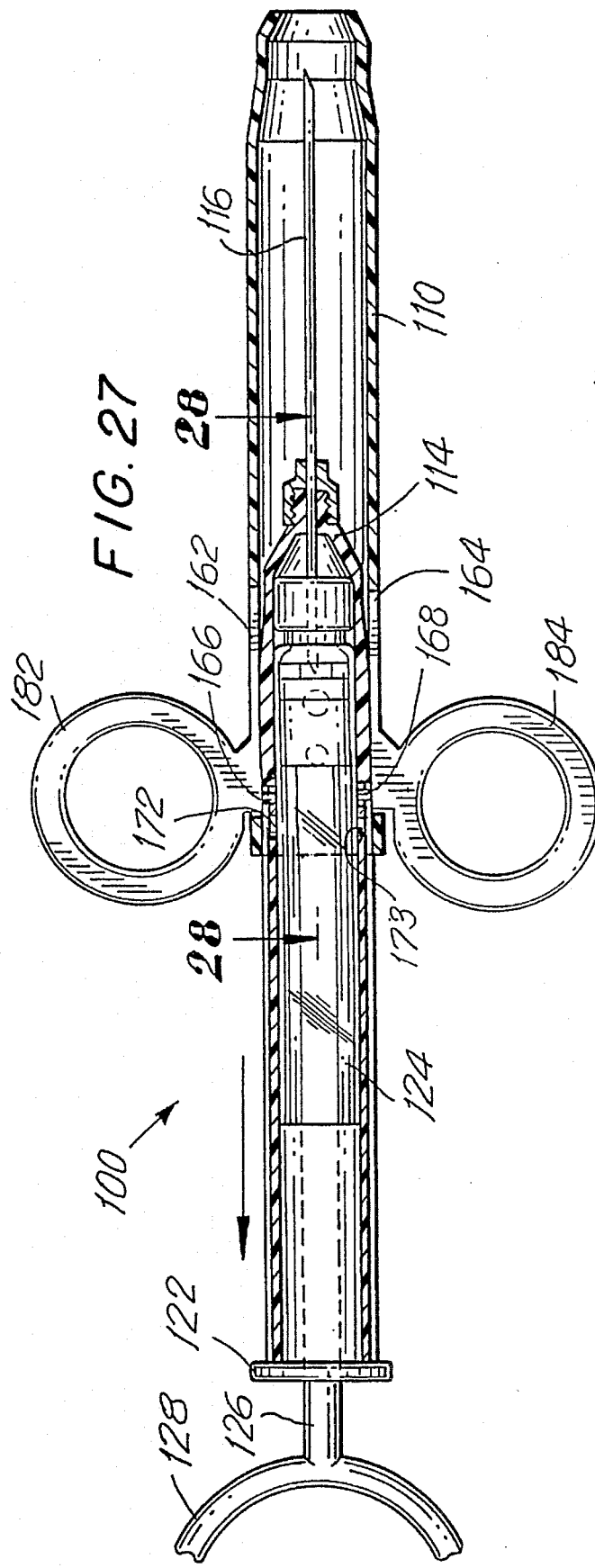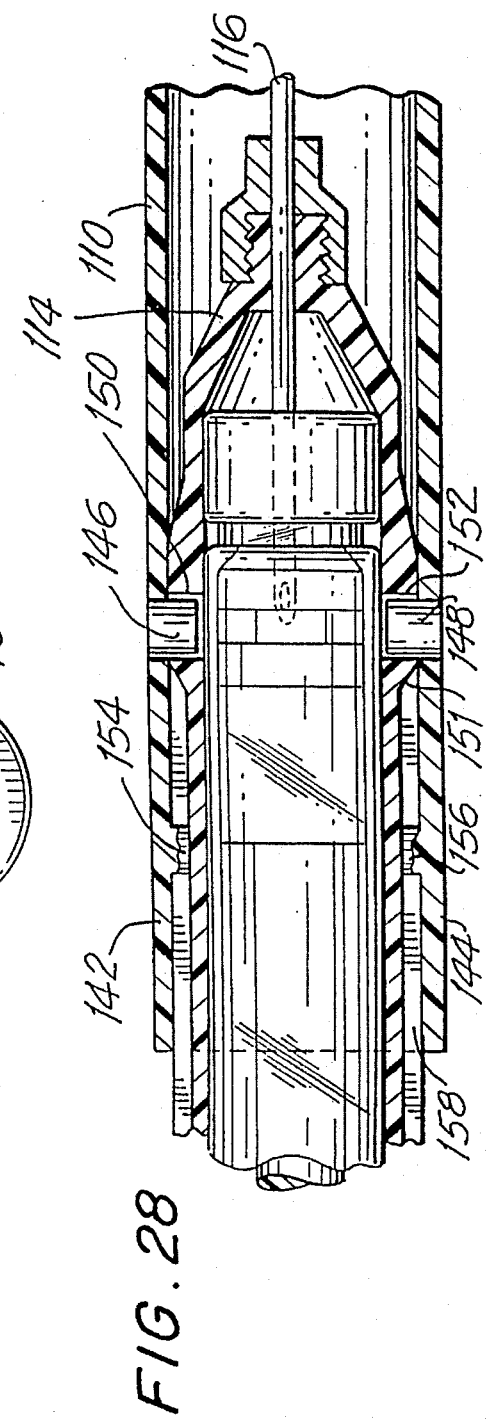
FIG. 27
FIG. 28

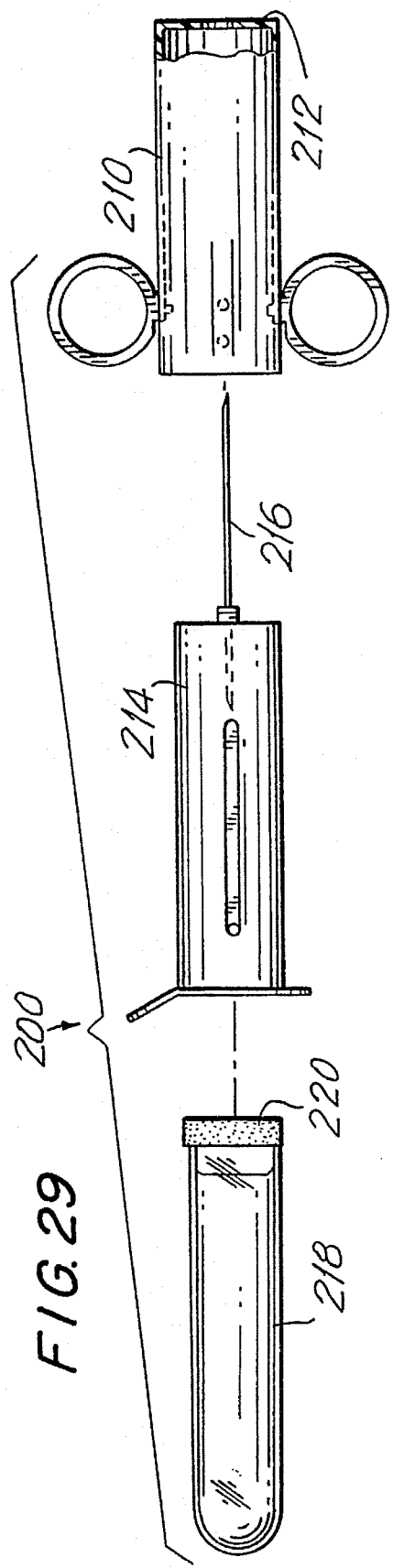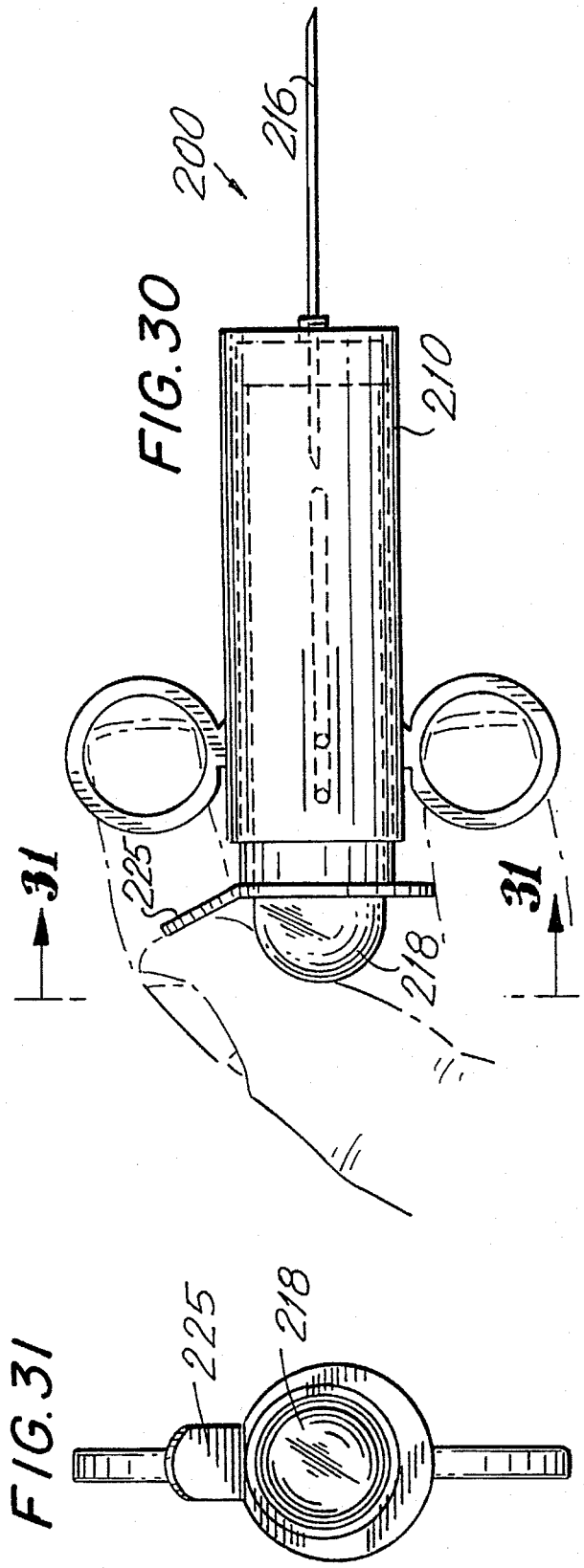
FIG. 29
FIG. 30
FIG. 31

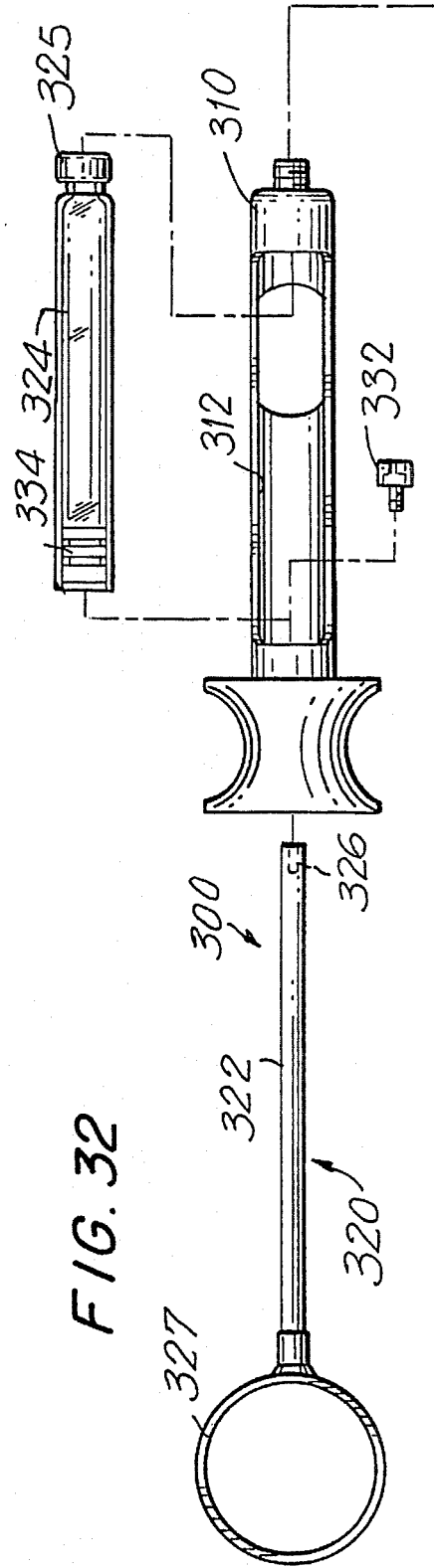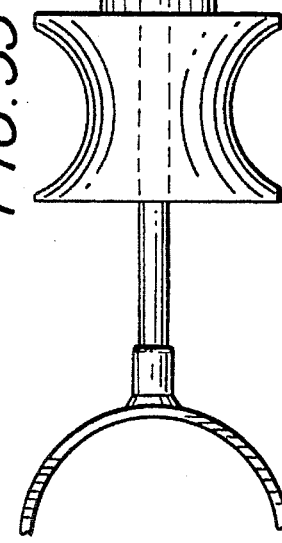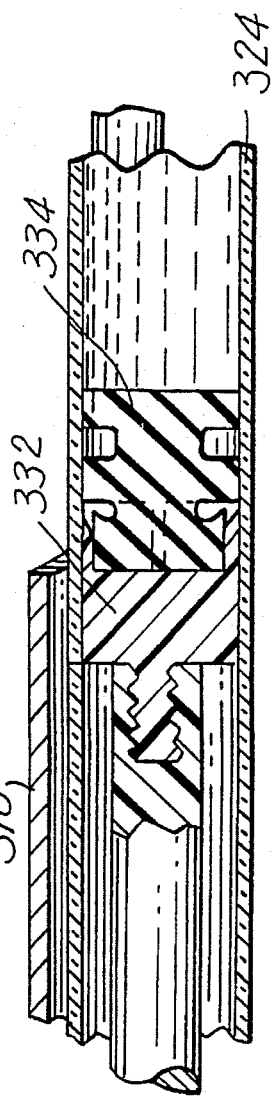

SAFETY SYRINGE

CROSS-REFERENCE TO RELATED APPLICATIONS

This application is a continuation-in-part of copending application Ser. No. 07/679,753, filed Apr. 3, 1991, now U.S. Pat. No. 5,306,258, and relates to Disclosure Document 342,262, filed Oct. 7, 1993.

BACKGROUND OF THE INVENTION

1. Field of the Invention

The subject invention relates to a syringe, and more particularly, to a safety syringe having a protective sheath configured to be locked in a secure position to cover a needle after utilization and prevent unwanted contact therewith.

2. Background of the Prior Art

Protection for medical personnel from inadvertent contact with contaminated syringe needles has become an increasing concern particularly because of the severity of certain infectious diseases which have developed. For example, the AIDS virus has been shown to be spread to persons who come into contact with a contaminated needle after the needle was used for a patient carrying the virus.

Numerous attempts have been made to protect medical personnel, patients and anyone in the area when syringes are used by providing various shielding devices for the needles. For example, U.S. Pat. No. 4,969,877 relates to a syringe which includes an outer casing into which the needle may be retracted after use. U.S. Pat. No. 4,973,316 relates to a one handed retractable sheath safety syringe. A number of other attempts at providing protection for safety syringe needles have been made.

None of the safety devices developed to date provide relatively simple and quick one hand application whereby the user may simply slide a protective device into several positions with one position being a locked position which is irreversible by normal action of the user. Further, there remains a need for such safety syringes which would be usable as an injecting syringe or as an aspirating syringe, all with one hand operation, while being simply automatically convertible to a configuration whereby the needle is covered and protected while preventing inadvertent re-exposure of the needle. The present invention provides such a safety syringe.

SUMMARY OF THE INVENTION

A syringe is provided which comprises a needle body having a proximal end and a distal end, a needle attached to the distal end of the needle body, means for drawing fluid into the needle body through the needle, and a protective sheath configured and dimensioned to be positioned about the needle body and movable between a first distal position whereby the needle is shielded by the sheath and a proximal position whereby the needle is exposed. The syringe includes means to releasably retain the protective sheath in the first distal position, means to releasably retain the protective sheath in the proximal position, and means to retain the protective sheath in a second distal position after use whereby the needle is protected by the sheath. Preferably, the sheath automatically becomes locked in the second distal position when it is moved to this position.

In a preferred embodiment the needle body has a proximal end and a distal end and defines a fluid chamber. The needle is attached to the distal end of the body and communicates with the fluid chamber. Means is provided for manually drawing fluid into the chamber through the needle and the protective sheath is positioned about the needle body and movable between a first distal position whereby the needle is shielded by the sheath and a proximal position whereby the needle is exposed. Means to releasably retain the sheath in the first distal position is provided and means to releasably retain the protective sheath in the proximal position is provided. The syringe includes means to lockingly retain the protective sheath in a second distal position, the second distal position being distal of the first distal position whereby the needle is protected from unwanted contact after use.

Preferably the needle body is an elongated cylindrical member defining the inner fluid chamber and the fluid chamber is cylindrically shaped. A plunger assembly is positioned within the inner fluid chamber for drawing or expelling fluids with respect thereto. The needle body includes a plurality of slots dimensioned, positioned and configured for reception of correspondingly shaped pegs which extend inwardly of the protective sheath to retain the sheath in at least one of a plurality of selective positions relative to the needle body.

At least two of the slots in the needle body are positioned in the proximal portion of the needle body and are configured for reception of at least two correspondingly dimensioned pegs on the safety sheath to retain the safety sheath in the proximal position relative to the needle body whereby the needle is exposed for use. At least two of the slots are positioned in the distal portion of the needle body and are configured for reception of at least two correspondingly dimensioned pegs on the safety sheath to retain the safety sheath in the first distal position relative to the needle body, whereby the needle is covered. Further, at least two of the slots in the needle body are positioned distally of the first mentioned distal slots for reception of at least two of the pegs on the safety sheath, the pegs being dimensioned, positioned and configured to lockingly retain the safety sheath in the second distal position relative to the needle body.

The slots which retain the safety sheath in the second distal position are configured to retain the correspondingly configured and positioned locking pegs on the safety sheath in a manner whereby the locking pegs are not removable from the slots by normal action of the user. Further, the locking slots in the needle body are each positioned adjacent and distal of a ramped surface thereon, the ramped surface being adapted and configured for slidable reception of the locking pegs on the safety sheath to facilitate slidable entry of the locking pegs into the locking slots positioned distally of the ramped surfaces. The locking pegs on the safety sheath include a ramped surface substantially parallel to the ramped surface on the needle body to facilitate slidable engaged reception of the locking pegs into the locking slots.

In the safety syringe according to the invention, the locking pegs are attached to the safety sheath in a manner to be resiliently movable in a direction away from the needle body such that the pegs are resiliently biased in a direction toward the locking slots on the needle body to lock the position of the safety sheath in the second distal position. The ramped surface on the needle body extends in a direction radially outwardly of the needle body from the proximal end to the distal end of the ramped surface. The ramped surface on the peg attached to the safety sheath extends in a direction radially outward toward the inner surface of the safety sheath in a direction from the proximal end to the distal end of the ramped surface. Further, the safety sheath is constructed of a resilient plastic material and the locking pegs are attached to strips formed integrally with the safety sheath and are adapted to be resiliently biased inwardly toward the safety sheath. The plastic material is transparent or translucent but may be opaque if desired. Such plastics as polyethylene polypropylene and polycarbonate are contemplated, but other suitable materials may be used.

The safety sheath includes two elongated strips attached to the safety sheath at their distal ends and resiliently biased inwardly toward the safety sheath. Also two similar locking strips are attached at their proximal ends and include the locking pegs.

Each elongated strip has an endless circular loop positioned at the proximal end, each loop being dimensioned for reception of one of the user's fingers. A plunger assembly is positioned within the needle body and adapted for drawing fluids therein through the needle by vacuum or out of the needle body by pressure. A finger loop is connected to the plunger assembly for movement of the plunger assembly in distal and proximal directions. The needle body includes at least one guide track extending along the length thereof and dimensioned for slidable reception of a correspondingly dimensioned peg extending inwardly of the inner surface of the safety sheath to retain the relative angular orientation between the safety sheath and the needle body. Preferably, at least four of the guide tracks are provided on the safety sheath and at least four of the correspondingly positioned and dimensioned pegs are provided. The tracks and the pegs are distributed approximately equally about the needle body to maintain rigidity and minimize lateral play within the safety sheath and the needle body. The elongated strips and the finger loops are integrally molded with the safety sheath in a manner which facilitates outward movement of the strips with respect to the safety sheath while the distal end of the strips are integrally attached to the safety sheath. The proximal ends of the locking strips are integrally molded with the safety sheath.

A method is disclosed for using a syringe having a hollow medical needle whereby the needle is protected from contact therewith before and after use, comprising providing a safety sheath in a first distal position whereby the needle is shielded prior to use, releasing the safety sheath and moving same to a proximal position whereby the needle is exposed for use, and advancing the safety sheath to a second distal position whereby the needle is protected by the safety sheath, the safety sheath having means to be locked into the second distal position whereby movement of the safety sheath to a position proximal thereof by the user is prevented.

According to the method the syringe includes an elongated needle body and the needle is attached to the distal end thereof, the needle communicating with an inner chamber defined by the needle body for reception of fluids through the needle and the sheath is automatically and simultaneously locked in the second distal position when advanced thereby by the user. The needle body includes a plunger assembly therein for drawing fluids into and discharging fluids out of the chamber.

An alternative safety syringe constructed in accordance with a preferred embodiment of the subject invention is provided which comprises a cylindrical sheath defining an axial bore and opposed proximal and distal end portions, a needle body dimensioned and configured to translate within the axial bore of the sheath, a needle extending from a distal end of the needle body, and a plunger assembly associated with the needle body for expelling fluid from the needle body and for drawing fluid into the needle body. A locking mechanism is provided for securing the needle body relative to the sheath in a locked position wherein the needle is shielded by the sheath. The locking mechanism includes a pair of opposed flexible locking struts formed monolithically with the sheath adjacent the proximal end portion thereof. The locking struts are fixed to the sheath at respective proximal and distal ends thereof. At least one locking peg extends radially inward from each of the flexible locking struts and a pair of opposed locking ports are defined in the needle body for receiving the locking pegs to secure the needle body in the locked position, thereby shielding the needle to prevent unwanted contact therewith.

The safety syringe further comprises means for releasably securing the needle body in a first position wherein the needle is retracted within the distal end portion of the sheath prior to utilization and a second position wherein the needle is protracted from a distal end portion of the sheath for utilization. Preferably, the releasable securing means comprises a pair of opposed deflectable locking strips formed monolithically with the sheath adjacent the proximal end thereof. Each locking strip includes an engagement peg which extends radially inward therefrom for engaging corresponding reception ports defined in the needle body. Means are also provided on each of the locking strips for facilitating engagement by a user's finger.

The safety syringe further comprises means for guiding the translation of the needle body with respect to the sheath. The guiding means includes at least one guide pin extending radially inward from the sheath and at least one elongate guide track formed on the needle body for cooperating with the guide pin. The guide pin and guide track also cooperate to maintain the angular orientation of the needle body with respect to the sheath.

Another safety syringe constructed in accordance with a preferred embodiment of the subject invention is provided which is configured to expel fluid from a cartridge having a piercable seal at a distal end thereof and a movable plug member disposed within a proximal end thereof. The syringe comprises a body defining an axial chamber for supporting the cartridge, a needle mounted to a distal end of the body having a proximal portion extending into the body for piercing the seal, a plunger associated with the body for urging the plug member in a distal direction to expel fluid from the cartridge into the needle, and means associated with the plunger for circumferentially engaging the plug member to ensure that an equal distribution of compressive forces is exerted upon the plug member during utilization.

The plug engaging means comprises a cylindrical hub configured to surround at least a portion of the plug member. Preferably, the hub includes at least one longitudinally extending slit for facilitating radial expansion of the hub, and the hub is preferably releasably fastened to a distal end of the plunger.

These and other features of the subject invention will become more readily apparent to those having ordinary skill in the art from the following detailed description of the invention taken in conjunction with the drawings.

BRIEF DESCRIPTION OF THE DRAWINGS

Preferred embodiments of the invention are described hereinbelow with reference to the drawings wherein:

FIG. 1 is a side view of the safety syringe constructed according to the present invention with the safety sheath in the distal position protecting the needle from unintended contact;

FIG. 2 is a top view of the safety syringe shown in FIG. 1;

FIG. 3 is a side view of the syringe shown in FIG. 1 with the safety sheath released and partially withdrawn to expose the needle;

FIG. 4 is a top view of the syringe shown in FIG. 3;

FIG. 11 is a top view of the needle body with major portions removed, illustrating the relative positions of the slots in the needle body on one side which are associated with the safety locking system;

FIG. 12 is a side elevational view thereof, illustrating the safety locking system according to the invention with the relative positions between the safety sheath and the needle body shown in the initial position corresponding to FIG. 1;

FIG. 13 is a side cross-sectional view thereof, illustrating the relative positions of the safety sheath and needle body after the safety sheath has been partially withdrawn;

FIG. 14 is a side cross-sectional view thereof, illustrating the relative positions of the safety sheath and needle body in position for use of the syringe either as an injecting or a fluid aspirating syringe;

FIG. 15 is a side cross-sectional view thereof illustrating the relative positions of the safety sheath and needle body shown in FIG. 14 after use, with the safety sheath pushed distally to a position just prior to engagement of the safety locking system;

FIG. 16 is a side cross-sectional view thereof illustrating the needle body and the safety sheath with the safety sheath just distally of the position shown in FIGS. 1 and 2;

FIG. 18 is a perspective view of another safety syringe constructed in accordance with a preferred embodiment of the subject invention with parts separated for ease of illustration;

FIG. 19 is a perspective view of the safety syringe of FIG. 18 with the needle disposed in a retracted position prior to utilization;

FIG. 20 is a cross-sectional view taken along line 20—20 of FIG. 19 illustrating the interaction between the needle body and the sheath;

FIG. 22 is a cross-sectional view taken along line 22—22 of FIG. 21 illustrating the locking pegs of the sheath disposed in an unlocked position corresponding to the needle being in a retracted position prior to utilization;

FIG. 24 is a cross-sectional view taken along line 24—24 of FIG. 23 illustrating the interaction between the needle body and the sheath when the needle body has been advanced in a distal direction to expose the needle for use;

FIG. 25 is a cross-sectional view taken along line 25—25 of FIG. 23 illustrating the position of the locking pegs of the sheath when the needle is protracted from the sheath for utilization;

FIG. 26 is a side elevational view in cross-section illustrating the plunger advanced in a distal direction to expel fluid from the cartridge supported within the needle body;

FIG. 27 is a side elevational view in cross-section illustrating the needle body disposed in a locked position wherein the needle is shielded by the sheath after utilization;

FIG. 28 is a cross-sectional view taken along line 28—28 of FIG. 27 illustrating the locking pegs on the sheath securely engaged within the locking ports defined in the needle body;

FIG. 29 is an exploded side elevational view of another safety syringe constructed in accordance with a preferred embodiment of the subject invention which is useful in drawing fluids into a specimen tube;

FIG. 30 is a side elevational view of the safety syringe of FIG. 29 with the specimen tube disposed within the needle body and the needle protracted from the sheath for utilization;

FIG. 31 is an elevational view of the proximal end of the safety syringe of FIG. 29 taken along line 31—31 of FIG. 30;

FIG. 32 is an exploded side elevational view of another safety syringe constructed in accordance with a preferred embodiment of the subject invention;

FIG. 33 is a side elevational view of the safety syringe of FIG. 32 in an assembled condition; and FIG. 34 is a cross-sectional view taken along line 34—34 of FIG. 33.

DETAILED DESCRIPTION OF THE PREFERRED EMBODIMENTS

Figure 5:
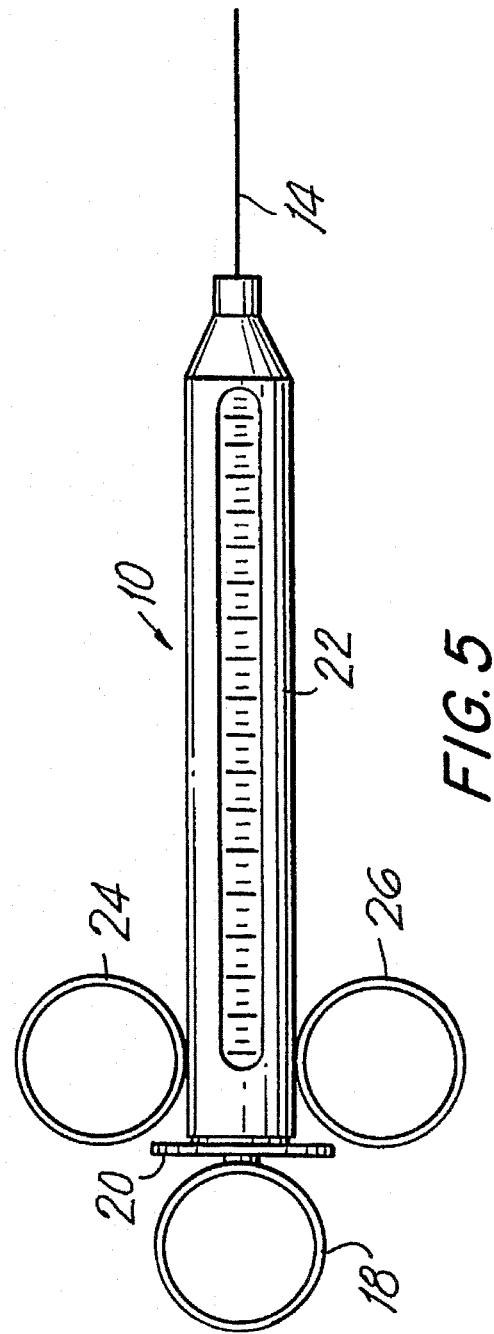
FIG. 5 is a side view of the safety syringe shown in FIG. 3 with the safety sheath locked in position in the fully withdrawn position to permit the syringe to be used normally.

In the description which follows "distal" means away from the user and "proximal" means toward the user.

Referring initially to FIG. 1 the safety syringe 10 constructed according to the present invention is shown. The syringe may be of the aspirating type or the injecting type. In the former, fluid is drawn from the body. In the latter, medication or other fluid is injected into the body by the needle. In either case, it is important to protect the needle after it has come in contact with the body fluids of the person in order to prevent inadvertent contact thereafter with a person other than the patient.

The safety syringe 10 includes a needle body 12 having a needle 14 at one end communicating with a chamber 16 defined internally of the needle body and shown in dotted lines. The needle is a medical or surgical type having a hollow cylindrical cross section for drawing and expelling liquids with respect to needle body 12. Finger loop 18 is attached to the needle body at a location just proximal of rear wall 20. A plunger 19 is shown schematically in dotted lines in FIGS. 1 and 4 and is connected to finger loop 18 by elongated member 21, also shown schematically.

As shown in FIG. 1, safety sheath 22 includes two finger loops 24, 26 attached to the sheath via relatively thin strips which are preferably formed of resilient material integrally with sheath 22 and which bias the loops inwardly toward the body to the position shown in FIG. 1. Preferably the safety sheath 22 is constructed of a transparent or translucent resilient plastic material and formed as a cylindrical tubular member having resilient strips 28,30 which are separable from the body of the safety sheath and are attached at the distalmost portion shown at 32. Although the strips are integrally molded as part of the safety sheath, they are actually separated from the main sheath by molded "cuts" shown at 30a in FIG. 2, which define the strips and permit the strips to be moved manually toward and away from the sheath. Further, as seen in FIGS. 1 and 2, the safety sheath is generally cylindrical and has portions of the cylindrical wall eliminated as shown at 22a to permit viewing of the transparent liquid contained in the needle body. Such plastic materials as polyethylene, polypropylene, or polycarbonates such as LEXAN brand material marketed by General Electric Company, Pittsfield, Mass., are contemplated. As noted, preferably, the sheath and the body are integrally molded as shown from such plastic materials.

Figure 17:
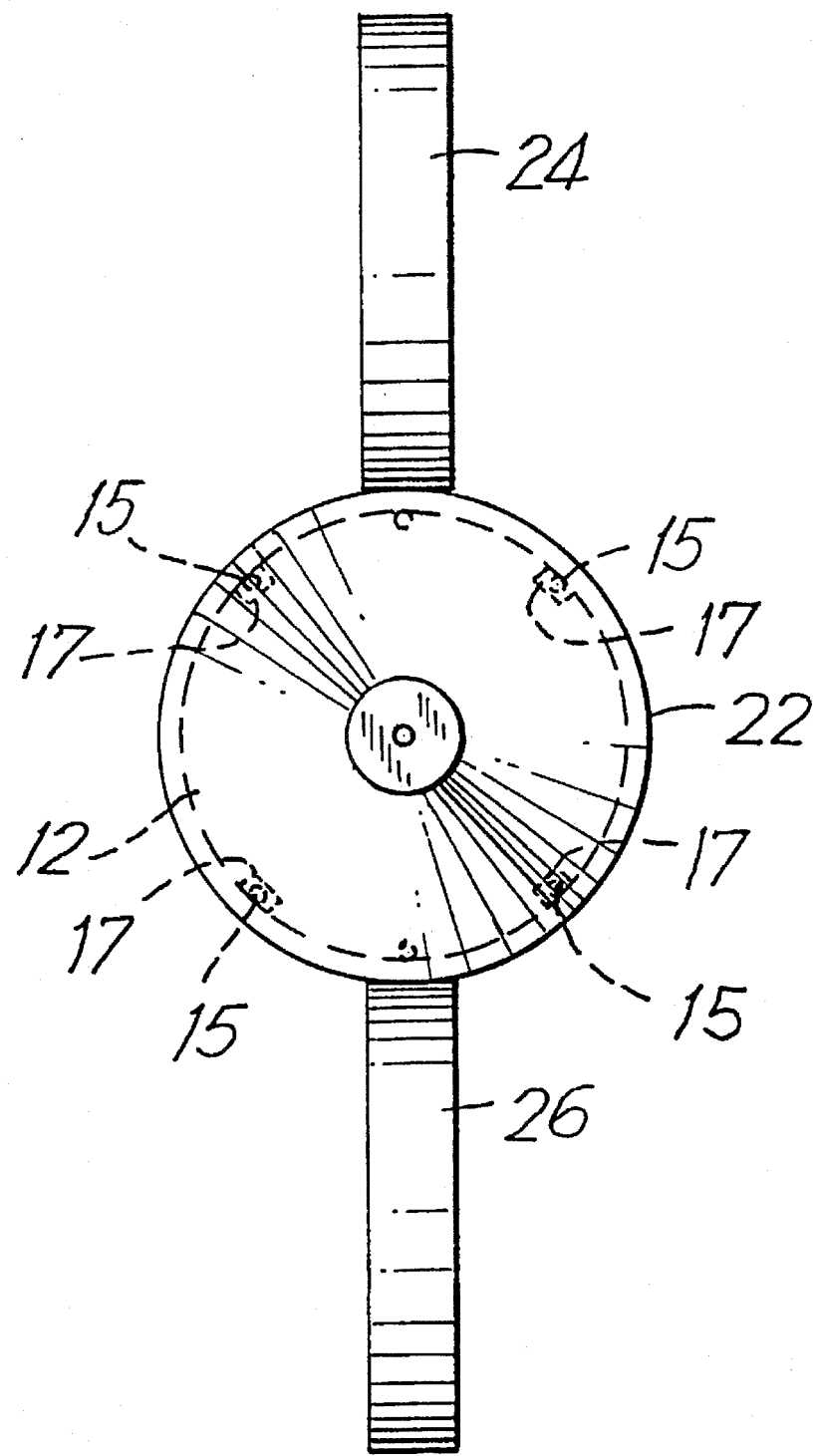
FIG. 17 is a proximal end view of the safety syringe shown in FIG. 5 with the rear wall and thumb ring removed.

The sheath 22 is dimensioned and configured to slide between proximal and distal positions relative to body 12. As best seen in FIG. 17, four tracks in the form of elongated slots 17 are formed in body 12 and four corresponding pegs 15 extend inwardly from the inner wall of the sheath 22 and are slidably positioned within tracks 17 to retain the relative angular orientation of sheath 22 with respect to body 12. In FIGS. 1 and 2 only two of such tracks 17 are shown. The normal pre-use condition of the syringe is as shown in FIG. 1.

Figure 6:
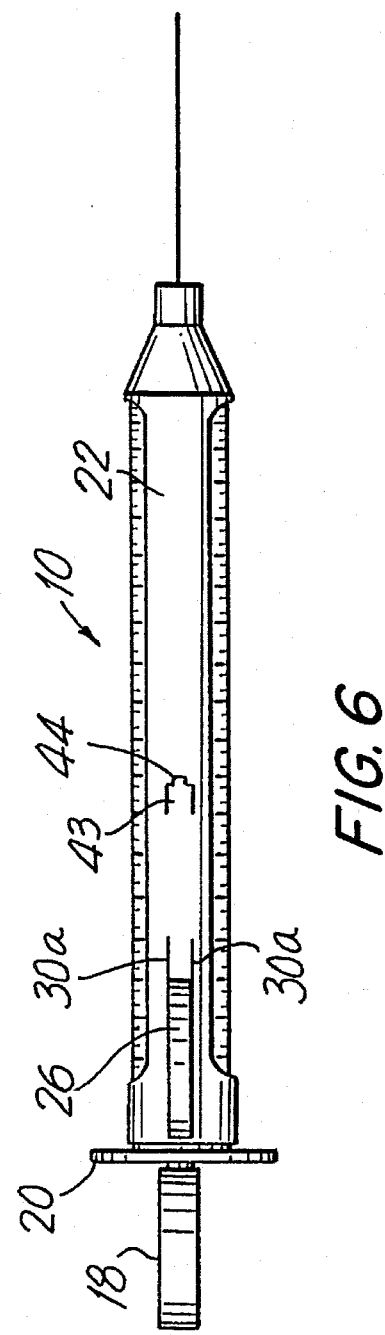
FIG. 6 is top view of the safety syringe shown in FIG. 5.

In FIGS. 3 and 4 the body 16 is shown after the safety sheath 22 has been partially withdrawn proximally by the user by placing the index and middle finger into the finger loops 26,24 and separating the loops as shown to release pegs 42 from peg reception notches 36 shown in FIG. 11. During this motion the user's thumb is positioned within finger loop 18. The safety sheath 22 is withdrawn fully to the proximalmost position shown in FIGS. 5 and 6 when finger loops 24,26 are permitted to return to their inwardly biased positions. At this time, pegs 42 enter slots 34 and thereby fix the position of the safety sheath 22 relative to the body 12 in the needle exposed condition shown in FIGS. 5 and 6.

Figure 7:
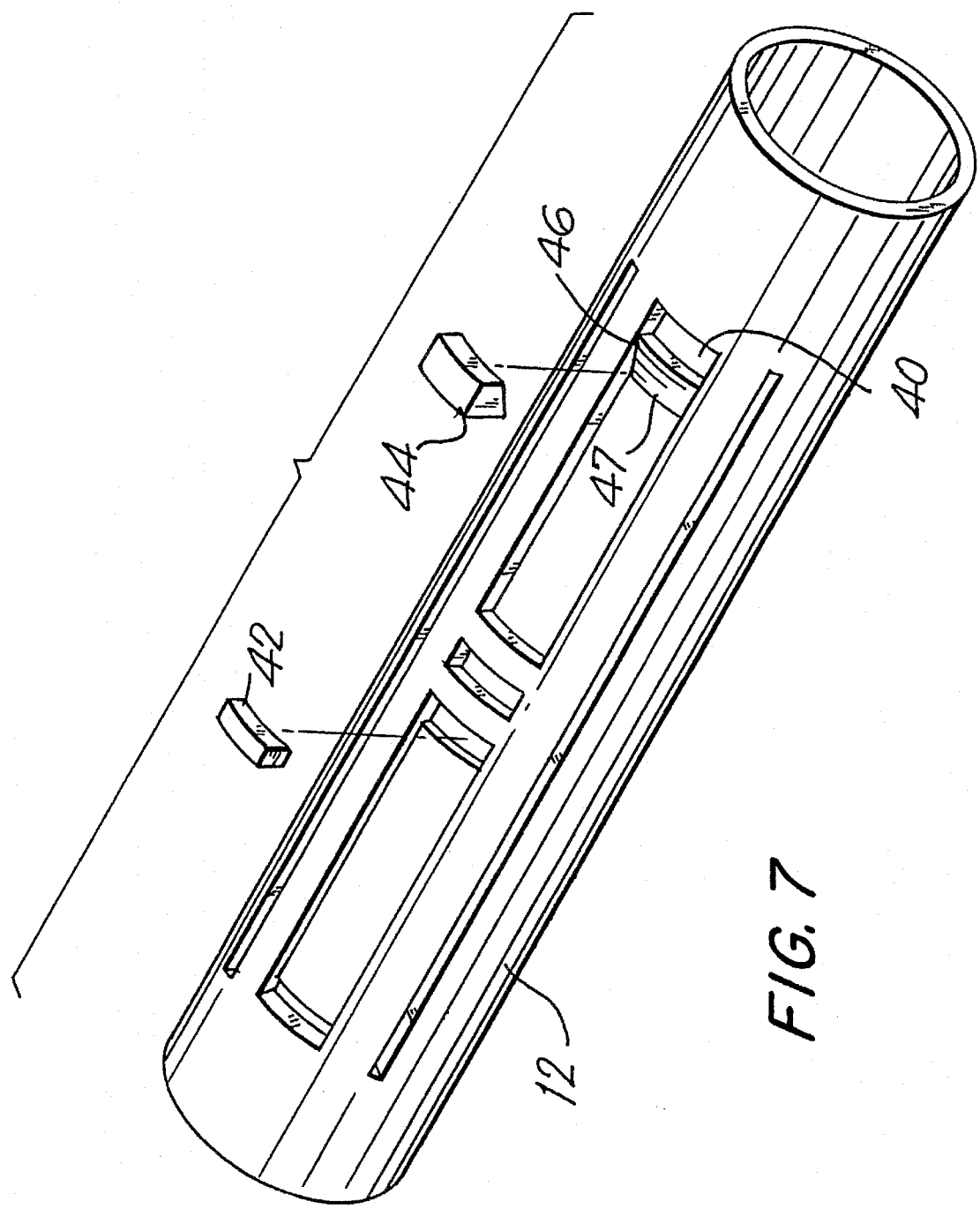
FIG. 7 is a perspective view with parts removed, illustrating schematically, one side of the body of the syringe constructed according to the present invention and the locking system for the safety syringe.
Figure 8:
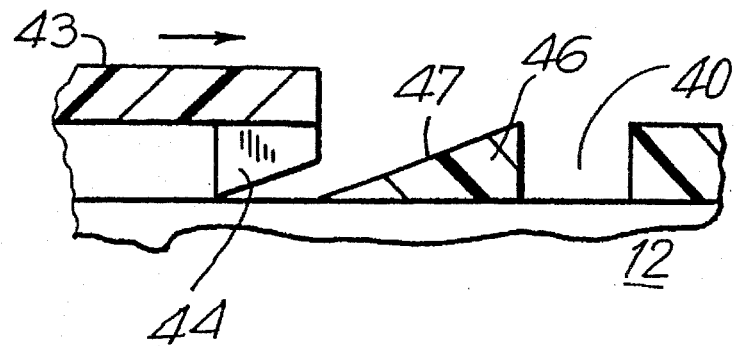
FIG. 8 is a greatly enlarged cross-sectional view illustrating the sheath safety locking mechanism as the safety sheath is being moved distally after using the syringe.
Figure 9:
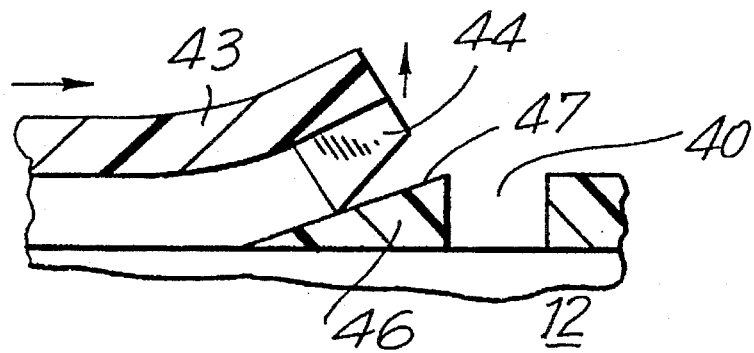
FIG. 9 is a greatly enlarged cross-sectional view of the safety locking mechanism shown in FIG. 8 just prior to locking the safety sheath in the protective position over the needle.

The system for releasably retaining the safety sheath 22 in the pre-use condition and the final safety locking system will now be described in connection with FIGS. 7, 8 and 11–16. In connection therewith for convenience of illustration in FIGS. 11–16 the locking system associated with one finger ring 24 will be described. In FIG. 7, the finger rings 26 and 24 and the remaining portions of the needle body 12 and sheath 22 have been removed for illustration purposes. As constructed, the locking system for the other finger ring 26 is identical but opposite in configuration and position to the system associated with the finger ring 24.

Body 12 includes a series of slots 34, 36, 38, 40 as shown in FIG. 11. Beneath finger ring 24 is positioned peg 42 adapted to enter into either of slots 34,36 or 38 to establish the position of the safety sheath 22 relative to the body 12. Third, or locking peg 44 is positioned on the internal wall of the sheath 22 and is configured to enter the distal slot 40 of the needle body. Locking peg 44 is attached to strip 43 which is cut out of the safety sheath 22 such that the peg 44 is resiliently biased toward the body 16 caused by the inward bias of strips 28, 30. This bias is due to the natural resilience of the plastic material forming the sheath 22 from which the sheath 22 and strips 28,30 are integrally molded. Just proximal of the distal slot 40 is a ramped member 46 for slidable contact by locking peg 44 and reception of peg 44 into slot 40 to lock and fix the position of the sheath in the distalmost, or needle protective position.

In operation, the safety syringe functions as follows. The syringe is delivered to the user in the configuration shown in FIG. 1 with the safety sheath 22 in the distal position corresponding to peg 44 being positioned as shown in FIG. 12 while peg 42 immediately beneath ring 24 being positioned within slot 36. Distal or proximal movement of sheath 22 is thus prevented by the position of peg 42 within slot 36.

To retract the sheath the user positions the thumb within finger loop 18 and the index and middle fingers respectively in one of the aspirating loops 24,26 as described previously. Thereafter, the index finger and middle finger are separated in opposite directions to release pegs 42 from slots 36 as shown in FIGS. 3, 4 and 13. The finger motion which releases the pegs is opposite the inward natural resilient force provided by strips 28,30 as shown in FIG. 3, which are formed out of sheath 22 and are resiliently biased toward the body 12. The configuration of body 12 is shown clearly in FIG. 7. The side not shown is the same. As will be observed from the drawings, after the pegs 42 are released the sheath is now free to travel in a proximal direction to expose the needle.

Upon withdrawing the sheath proximally to the position shown in FIG. 14 finger loops 24,26 are returned to the normal inward positions and pegs 42 re-enter the rearwardly positioned slots 34 thereby fixing the position of sheath 22 with respect to body 12 and exposing needle 14 for use. At this point, the needle may be inserted into the patient's body and the thumb ring 18 may be withdrawn to withdraw the internal plunger assembly 19 of the needle body for normal use of the syringe as an aspirating device, i.e. to draw fluid from the body. Alternatively, this motion may be used to draw fluid from a separate source—such as medication vial—for injection into the body as shown in FIG. 12. When the syringe is in the normal use condition with pegs 42 within slots 34, the distal locking pegs 44 are in a position just proximal of ramp 46 and distal locking slot 40 as shown in FIG. 12.

Figure 10:
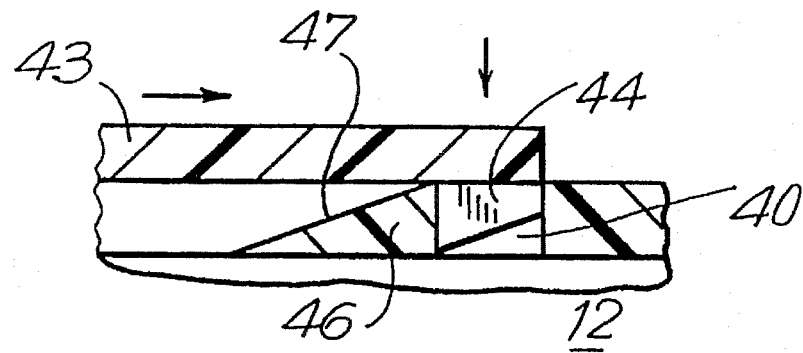
FIG. 10 is a greatly enlarged cross-sectional view of the safety locking mechanism shown in FIGS. 8 and 9 when the safety sheath has been moved distally to the needle protective distalmost position preventing further needle use.

After normal use of the syringe the aspirating finger loops 24,26 are once again separated laterally by the index and middle fingers to release pegs 42 from the proximal slots 34 freeing the sheath for distal movement to a distal position covering needle 14 and corresponding to the position of peg 44 within slot 40 as shown in FIG. 10. During this movement, peg 44, which is ramped oppositely—and preferably approximately parallel—to ramp 46 as shown, slides over ramp surface 47 of ramp 46 and drops into slots 40 under the natural inward resilient bias provided by the resilient material of strip 43. Resilient strips 43 are preferably integrally molded with sheath 22 similarly to strips 28,30. They are essentially separated from sheath 22 by cuts in the same manner as strips 28,30 to bias pegs 44 inwardly toward body 12. When the pegs 44 are positioned within slots 40 the proximal pegs 42 will be positioned within slots 38, the positions of which are just distal of the initial slots 36. As noted, since the pegs 44 are also positioned within slots 40 which are located just distally of the initial position of pegs 44 shown in FIG. 12, the distal position of sheath 22 will be fixed relative to the body 12.

It will be appreciated from the view shown in FIGS. 10 and 16 of the pegs 44 within slots 40 that the configuration of the pegs 44 are such that sheath 22 is locked into a distal needle protective position just slightly distal of the initial position shown in FIG. 1. The resilient action of the material of the strips 43 which cause pegs 44 to become locked within slots 40 render the sheath 22 immovable under normal use by the user. Withdrawal of safety sheath 22 from this locked position is virtually impossible forcing pegs 44 outwardly of slots 40 against the inward resilient force of strips 42. In any event, normal user motions will not release the safety sheath. Thus, the needle is protected by the position of the sheath and inadvertent contact with the known user or other party is virtually impossible without forcing the pegs 44 out of slots 40 or physically destroying the safety sheath 22.

Referring to FIGS. 18 and 19, another safety syringe constructed in accordance with a preferred embodiment of the subject invention is illustrated and is designated generally by reference numeral 100. In brief, safety syringe 100 comprises a cylindrical sheath 110 having an axial bore 112 extending therethrough for receiving a generally cylindrical needle body 114. A needle 116 is releasably fastened to the distal end of needle body 114 and includes a proximal portion 116a which extends into needle body 114 for interacting with a medicament cartridge 124, and a distal portion 116b for delivering medicament to a patient.

A plunger assembly 120 is operatively associated with needle body 114 and is mounted thereto through a cylindrical fitting 122. Plunger assembly 120 is adapted to expel medicament from a cartridge 124 and includes an elongated shaft 126 having a thumb ring 128 at a proximal end thereof and a threaded bore 130 at a distal end thereof for receiving a cylindrical hub 132. Hub 132 is dimensioned and configured to engage an elastomeric plug 134 which is operatively associated with medicament cartridge 124, as best seen in FIG. 25.

An inwardly tapered leading edge 136 is defined on hub 132 for facilitating engagement with plug 134, and opposed longitudinally extending slits 138a and 138b are formed in the wall of hub 132 for facilitating radial expansion of hub 132 during engagement with plug 134. A threaded stem 140 extends from a proximal end of hub 132 for threadably engaging bore 130 at the distal end of plunger shaft 126. Alternatively, hub 132 can be formed monolithically with the elongated shaft 126 of plunger assembly 120.

It will be appreciated that, during an injection, the plug should follow a precise center line of the cartridge. However, if the plug should become skewed, a localized build-up of pressure can occur causing the cartridge to break. Accordingly, hub 132 is provided to ensure that an evenly distributed compressive force is exerted upon plug 134 by plunger assembly 120 during utilization to maintain the centered orientation of plug 134. In addition, the hub is atraumatic in configuration, and, unlike with conventional syringes which employ aspiration hooks for interacting with the cartridge plug, the hub 132 is less likely to cause an injury to a user.

Referring to FIG. 20, safety syringe 100 further comprises a locking mechanism for securing sheath 110 in a locked position with respect to needle body 114. In this locked position, which is illustrated in FIG. 27, needle 116 is shielded by sheath 110 to prevent unwanted contact therewith after an injection. The locking mechanism includes opposed flexible locking struts 142 and 144 which are preferably formed monolithically with sheath 110 adjacent the proximal end thereof and which are fixed at respective distal and proximal ends thereof. Locking struts 142 and 144 include respective radially inwardly extending locking pegs 146 and 148 for positively engaging corresponding locking ports 150 and 152 in needle body 114, as best seen in FIG. 28. The locking ports have ramped proximal edges 151 for facilitating engagement, as best seen in FIG. 18. When locking pegs 146 and 148 are engaged within locking ports 150 and 152, relative movement of needle body 114 and sheath 110 is inhibited, thereby preventing unwanted contact with needle 116.

Locking struts 142 and 144 are also provided with respective guide pegs 154 and 156, as shown for example in FIG. 22, which interact with corresponding guide tracks 158 and 160 defined in needle body 114 (see FIG. 25). Pegs 154 and 156 guide the longitudinal translation of sheath 110 with respect to needle body 114, and further maintain the angular orientation of sheath 110 with respect to needle body 114.

Figure 21:
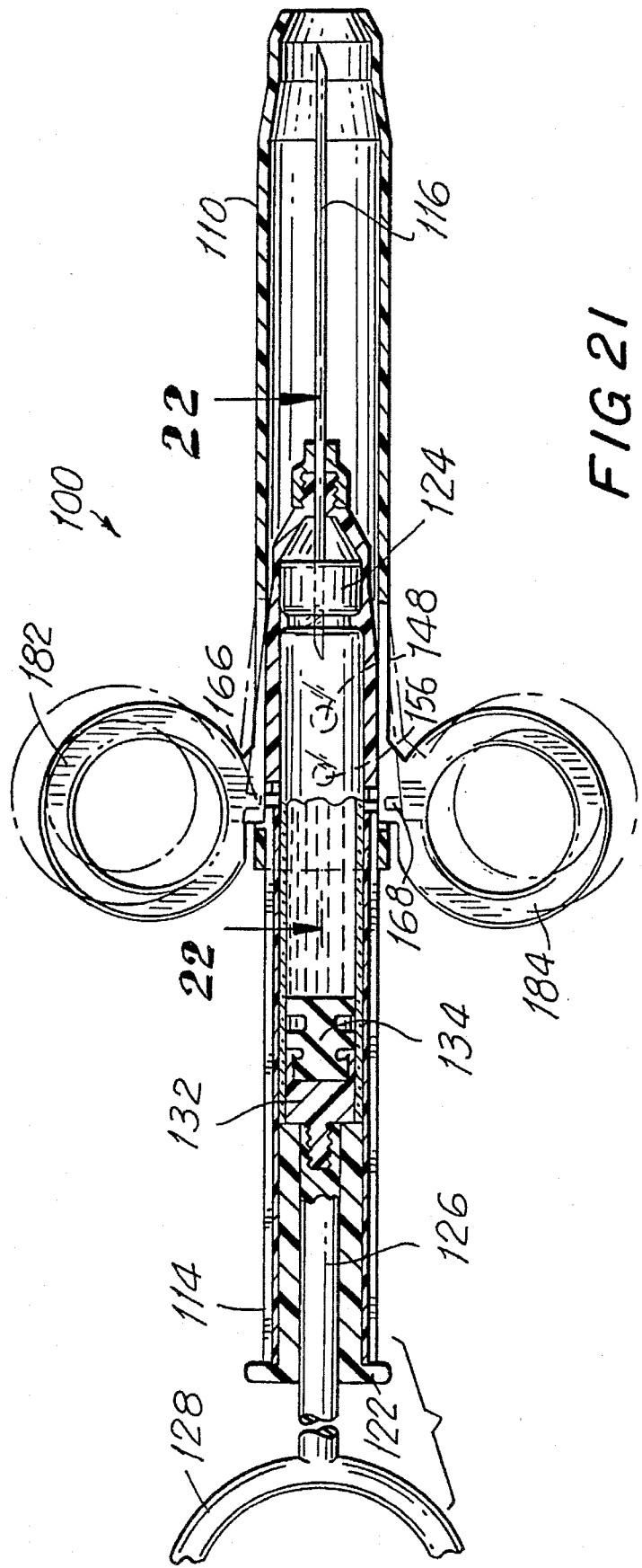
FIG. 21 is a side elevational view in cross-section taken along line 21—21 of FIG. 19 with the needle disposed in a retracted position and illustrating the releasable locking strips of the sheath in a deflected position.
Figure 23:
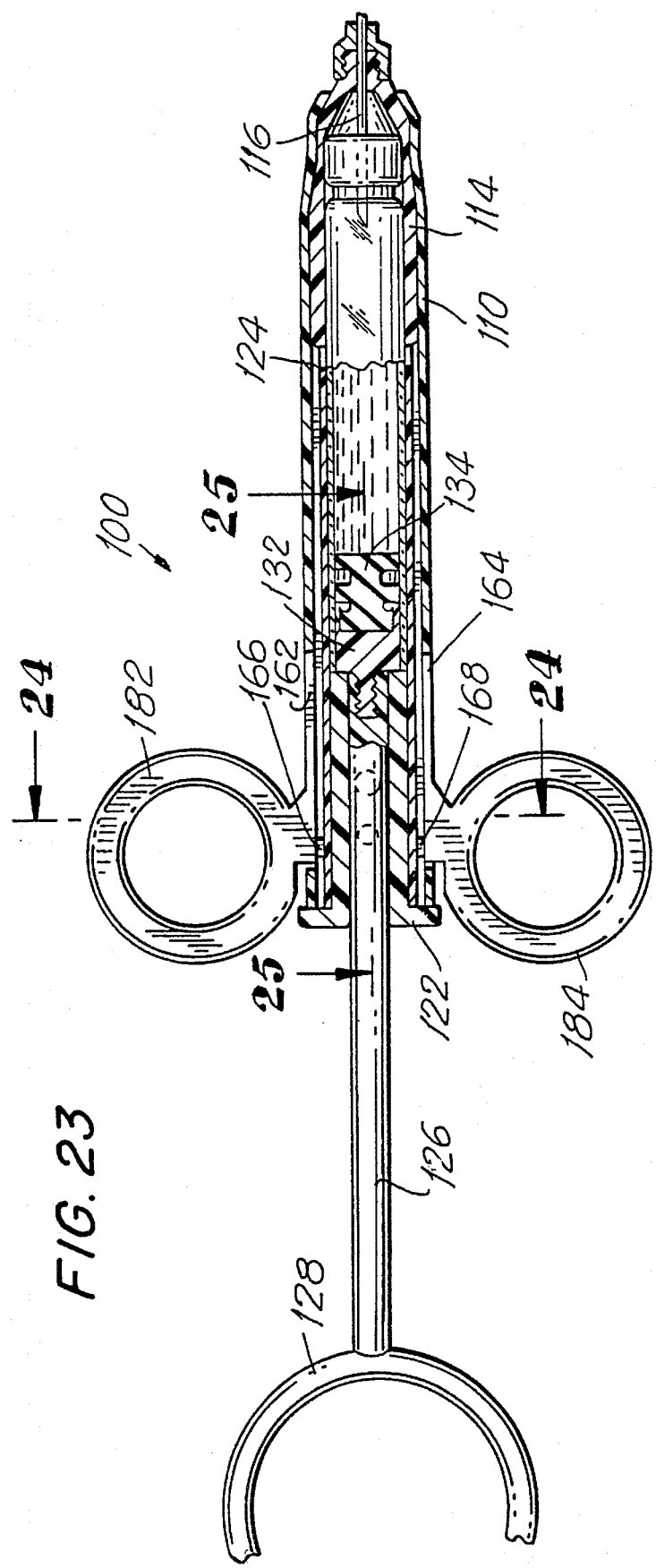
FIG. 23 is a side-elevational view in cross-section illustrating the needle body disposed in a distal position corresponding to the needle being protracted from a distal end of the sheath for utilization.

Safety syringe 100 further comprises a releasable locking mechanism for maintaining sheath 110 in a first distal position, shown in FIG. 21, wherein needle 116 is retracted within sheath 110 prior to utilization, and a second proximal position, shown in FIG. 23, wherein needle 116 is protracted from sheath 110 for performing an injection. The releasable locking mechanism includes a pair of opposed deflectable locking strips 162 and 164 formed monolithically with sheath 110 adjacent the proximal end thereof and are fixed to sheath 110 at respective distal ends thereof. Locking strips 162 and 164 are provided with respective engagement pegs 166 and 168, as shown for example in FIGS. 20 and 21, which releasably engage corresponding spaced apart reception ports formed in needle body 114 (see FIG. 26). In particular, as best seen in FIG. 26, engagement peg 166 is positioned to interact with first and second distal reception ports 170 and 172 and a proximal reception port 174. The distal-most reception port 170 corresponds to sheath 110 being disposed in a position wherein needle 116 is retracted within sheath 110 after use and sheath 110 is securely locked from movement with respect to needle body 114. Reception port 172 corresponds to sheath 110 being disposed in a position wherein needle 116 is retracted within sheath 110 prior to utilization. Proximal reception port 174 corresponds to sheath 110 being disposed in a position wherein needle 116 is protracted from sheath 110 for performing an injection.

In use, safety syringe 100 is employed by initially deflecting locking strips 162 and 164, utilizing finger rings 182 and 184, to release sheath 110 and permit the movement thereof, as shown for example in FIG. 21. At such a time, locking pegs 146 and 148 are disengaged from their respective locking ports 172 and 173 and the translation of sheath 110 may be guided by pegs 154 and 156. Furthermore, at such a time, as shown in FIG. 22, the proximal portion 116a of needle 116 has pierced through the distal seal 125 on medicament cartridge 124 to permit the expulsion of medicament therefrom.

Subsequently, a force is exerted upon plunger assembly 120 to move needle body 114 into a position wherein needle 116 is protracted from sheath 110, as shown for example in FIG. 23. At such a time, pegs 166 and 168 are engaged in respective proximal reception ports 174 and 175 and hub 132 is circumferentially engaged about plug 134 such that safety syringe 100 to perform an injection. Then, as illustrated in FIG. 26, the injection is performed by urging plunger assembly 120 in a distal direction so as to drive plug 134 through cartridge 124 to expel medicament therefrom.

As plug 134 is driven distally, hub 132 serves to maintain the centered orientation thereof within cartridge 124.

Following an injection, the deflectable locking strips 162 and 164 are once again moved radially outward from sheath 110 by the user to disengage pegs 166 and 168 from the position shown in FIG. 24, and permit relative movement of sheath 110 and needle body 114. As shown in FIG. 27, needle body 114 is then retracted in a proximal direction, through a sufficient distance to enable the engagement of locking pegs 146 and 148 within locking ports 150 and 152, as best seen in FIG. 28. Also, at such a time, engagement pegs 166 and 168 are received within respective distal reception ports 170 and 171.

Referring to FIGS. 29–31, another safety syringe constructed in accordance with a preferred embodiment of the subject invention is illustrated and is designated generally by reference numeral 200. Safety syringe 200 is adapted to collect blood samples through needle 216 and is substantially identical to safety syringe 100 in that it comprises a sheath 210 having a bore 212 extending therethrough, a needle body 214 configured to translate relative to bore 212, a locking mechanism for securing the sheath 210 relative to the needle body 214 after use, and a releasable locking mechanism for maintaining the sheath 210 in selected positions prior to and during utilization. In contrast to the safety syringe 100 described hereinabove, needle body 214 is configured to support a test tube 218 having a piercable seal 220 at the distal end thereof. Test tube 218 is a vaccum sealed tube for collecting blood samples from a patient. Safety syringe 200 also includes a thumb rest 225 at the proximal end of needle body 214 to facilitate proper handling of the syringe by the user.

Referring to FIGS. 32–34, there is illustrated another syringe constructed in accordance with a preferred embodiment of the subject invention designated generally by reference numeral 300. Syringe 300 includes a cylindrical body 310 having an internal chamber 312 for housing a medicament cartridge 324. A needle 316 is releasably mounted to a distal end of syringe body 310 and includes a proximal portion 316a for piercing a seal 325 disposed at the distal end of cartridge 324.

Syringe 300 further comprises a plunger assembly 320 including an elongated shaft 322 having a thumb ring 327 at a proximal end thereof and a threaded reception port 326 provided at a distal end thereof. A cylindrical hub 332 is threadably mounted in reception port 326 and is dimensioned and configured to circumferentially engage the elastomeric plug 334 which is disposed within the proximal end portion of medicament cartridge 324, as best seen in FIG. 34. As set forth hereinabove with respect to safety syringe 100, hub 332 serves to maintain the centered orientation of plug 334 as it is driven distally through cartridge 324.

Although the subject invention has been described with respect to a preferred embodiment, it will be readily apparent to those having ordinary skill in the art to which it appertains that changes and modifications may be made thereto without departing from the spirit or scope of the subject invention as defined by the appended claims.

What is claimed is:

1. A safety syringe comprising:
   a) an elongated sheath defining an axial bore and opposed proximal and distal end portions;
   b) a needle body mounted to translate within said axial bore of said sheath;
   c) a needle extending from a distal end of said needle body;
   d) a plunger assembly mounted for movement within said needle body; and
   a locking mechanism for securing said needle body relative to said sheath in a locked position wherein said needle is shielded by said sheath, said locking mechanism including:
   i) a pair of opposed flexible locking struts formed integral with said sheath, said locking struts each having opposed proximal and distal ends fixed to said sheath;
   ii) at least one locking peg extending radially inward from each of said flexible locking struts; and
   iii) a pair of opposed locking ports defined in said needle body for receiving said locking pegs to secure said needle body in said locked position.

2. A safety syringe as recited in claim 1, further comprising means for releasably securing said needle body in a first position wherein said needle is retracted within said distal end portion of said sheath prior to utilization and a second position wherein said needle is protracted from said distal end portion of said sheath for utilization.

3. A safety syringe as recited in claim 2, wherein said releasable securing means comprises a pair of opposed deflectable locking strips formed out of said sheath adjacent said proximal end portion thereof, said locking strips fixed to said sheath at respective distal ends thereof in a cantilevered manner and including means for releasably engaging said needle body.

4. A safety syringe as recited in claim 3, wherein said releasable engaging means includes an engagement peg extending radially inwardly from each of said deflectable locking strips for engaging corresponding spaced apart reception ports defined in said needle body.

5. A safety syringe as recited in claim 3, wherein each of said deflectable locking strips include means for facilitating engagement by a user's finger.

6. A safety syringe as recited in claim 1, wherein said needle body defines an axial cavity and a cylindrical cartridge containing a fluid for delivery through said needle is disposed therein.

7. A safety syringe as recited in claim 6, wherein said cartridge includes a piercable seal at a distal end thereof and a movable plug member disposed within a proximal end portion thereof.

8. A safety syringe as recited in claim 7, wherein said plunger assembly includes means for circumferentially engaging said plug member.

9. A safety syringe as recited in claim 1, further comprising means for guiding the translation of said needle body with respect to said sheath.

10. A safety syringe as recited in claim 9, wherein said guiding means includes at least one guide pin extending radially inward from said sheath and at least one elongate guide track formed on said needle body for cooperating with said guide pin, said guide pin and said guide track further cooperating to maintain the angular orientation of said needle body with respect to said sheath.

11. A safety syringe as recited in claim 1, wherein said plunger assembly is mounted for movement within said needle body for expelling fluid from said needle body or for drawing fluid into said needle body through said needle.

12. A safety syringe comprising:
   a) a cylindrical sheath defining an axial bore and opposed proximal and distal end portions;
   b) a needle body mounted to translate within said axial bore of said sheath;
   c) a needle extending from a distal end of said needle body, said needle body movable relative to said sheath between a first position wherein said needle is retracted within said distal end portion of said sheath prior to utilization and a second position wherein said needle is protracted from said distal end portion of said sheath for utilization;

d) a plunger assembly mounted for movement within said needle body for expelling fluid from said needle body or for drawing fluid into said needle body through said needle when said needle body is in said second position;

e) a locking mechanism for securing said needle body relative to said sheath in a third position wherein said needle is shielded by said sheath after utilization, said locking mechanism including:
  i) a pair of opposed flexible locking struts formed integral with said sheath, said locking struts each having opposed proximal and distal ends fixed to said sheath;
  ii) at least one locking peg extending radially inward from each of said flexible locking struts; and
  iii) a pair of opposed locking ports defined in said needle body for receiving said locking pegs to secure said needle body in said locked position; and f) means for releasably securing said needle body in said first position and said second position.

13. A safety syringe as recited in claim 12, further comprising means for guiding the translation of said needle body with respect to said sheath.

14. A safety syringe as recited in claim 13, wherein said needle body defines an axial cavity, and a cylindrical cartridge containing a fluid for delivery through said needle is disposed therein.

15. A safety syringe as recited in claim 14, wherein said cartridge includes a piercable seal at a distal end thereof and a movable plug member disposed within a proximal end portion thereof.

16. A safety syringe as recited in claim 15, wherein said plunger assembly includes means for circumferentially engaging said plug member.

17. A safety syringe as recited in claim 13, wherein said guiding means includes at least one guide pin extending radially inward from said sheath and at least one elongate guide track formed on said needle body for cooperating with said guide pin, said guide pin and said guide track further cooperating to maintain the angular orientation of said needle body with respect to said sheath.

18. A safety syringe as recited in claim 12, wherein said releasable securing means comprises a pair of opposed deflectable locking strips formed integral without of said sheath adjacent said proximal end portion thereof, said locking strips fixed to said sheath at respective distal ends thereof in a cantilevered manner and including means for releasably engaging said needle body.

19. A safety syringe as recited in claim 18, wherein said releasable engaging means includes an engagement peg extending radially inwardly from each of said deflectable locking strips for engaging corresponding spaced apart reception ports defined in said needle body.

20. A safety syringe as recited in claim 18, wherein each of said deflectable locking strips include means for facilitating engagement by a user's finger.

* * * * *